(12) United States Patent
Kneer

(10) Patent No.: US 6,837,865 B2
(45) Date of Patent: Jan. 4, 2005

(54) IMPLANT SYRINGE

(75) Inventor: Roland Kneer, Farchant (DE)

(73) Assignee: Gaplast GmbH, Altenau (DE)

( * ) Notice: Subject to any disclaimer, the term of this patent is extended or adjusted under 35 U.S.C. 154(b) by 193 days.

(21) Appl. No.: 10/168,236

(22) PCT Filed: Dec. 5, 2000

(86) PCT No.: PCT/DE00/04329

§ 371 (c)(1),
(2), (4) Date: Jun. 18, 2002

(87) PCT Pub. No.: WO01/43811

PCT Pub. Date: Jun. 21, 2001

(65) Prior Publication Data

US 2002/0193743 A1 Dec. 19, 2002

(30) Foreign Application Priority Data

Dec. 18, 1999 (DE) .......................................... 199 61 197

(51) Int. Cl.⁷ ............................................. A61M 31/00
(52) U.S. Cl. ........................ 604/57; 604/110; 604/218; 600/7; 222/386
(58) Field of Search ................................. 604/110, 263, 604/57–60, 181, 187, 197, 198, 218, 220, 227, 228, 232, 231; 600/3–5, 7, 8, 12; 222/386; 423/6.12

(56) References Cited

U.S. PATENT DOCUMENTS

| 4,185,619 | A | * | 1/1980 | Reiss ............................. 600/5 |
| 4,723,943 | A | * | 2/1988 | Spencer ...................... 604/198 |
| 4,936,627 | A | * | 6/1990 | Grimm et al. ................ 604/60 |
| 5,695,463 | A | * | 12/1997 | Cherif-Cheikh .............. 604/60 |
| 5,762,633 | A | * | 6/1998 | Whisson ..................... 604/187 |
| 6,478,768 | B1 | * | 11/2002 | Kneer .......................... 604/60 |

* cited by examiner

Primary Examiner—Nicholas D. Lucchesi
Assistant Examiner—Cris L. Rodriguez
(74) Attorney, Agent, or Firm—Pyle & Piontek

(57) ABSTRACT

An implant syringe including a guide sleeve which has seated therein a syringe needle arrangement composed of a syringe needle, a needle holder, a grip member and a preparation receiving member. The syringe needle arrangement is blocked in an initial state by two spring arms that are cut out from the guide sleeve and obliquely project inwards such that they rest on a rear wall of the syringe needle arrangement. When the plunger of the implant syringe is pushed forwards to advance the preparation up to the head end of the syringe, a sleeve which is connected to the plunger abuts on the spring arms and bends them outwards, whereby the syringe needle arrangement can be retracted. The two operations are carried out without changing the position of the hand, thereby simplifying the handling of the implant syringe.

5 Claims, 1 Drawing Sheet

IMPLANT SYRINGE

BACKGROUND OF THE INVENTION

The present invention relates to an implant syringe needle arrangement which is composed of a syringe needle, a projecting grip member and a preparation receiving member that are interconnected and seated in a guide means to perform a joint axial movement, and further comprising a plunger the advance movement of which towards the syringe needle is limited by an abutment such that a distance which is at least equal to the length of a preparation to be administered remains between the exit opening of the syringe needle and the head end of the plunger, the syringe needle arrangement being retractable by means of the grip member at least by a distance corresponding to the length of the preparation.

Such an implant syringe is used for administering an elongated strand-shaped preparation with a sustained release substance into a patient's body. Most of the time, the sustained release preparation is placed into the patient's abdominal wall into which a receiving channel for the preparation has previously been pierced by means of the syringe needle.

German Patent No. 197 34 385 C1 discloses an implant syringe of the above-mentioned kind. Said implant syringe is handled such that the insertion channel is first formed by piercing the syringe needle, for instance, into a patient's abdominal wall to such an extent that the front edge of a two-part guide sleeve of the implant syringe comes to rest on the patient's skin. After a spacer element has been removed, the plunger is then pushed forwards by a base plate gripping behind a spacer of the implant syringe and by exerting pressure on an end plate connected to the plunger. The plunger pushes the preparation forwards into the syringe needle until a sleeve connected to the plunger impinges on the base plate of the spacer.

Subsequently, the implant syringe is gripped on the front grip member and the base plate of the spacer, and the grip member is retracted up to an abutment. Upon impingement on the abutment the syringe needle is fully retracted from the preparation which is thereby deposited in the insertion channel, whereupon the implant syringe is removed.

With such an implant syringe a preparation, which need not necessarily have an elongated strand-shaped form, can be deposited exactly in the insertion channel, said operation being carried out without any pain—apart from the formation of the insertion channel. A drawback of the known implant syringe is that the syringe needle must be gripped around for retraction of said needle, which renders the handling of the syringe difficult.

SUMMARY OF THE INVENTION

It is the object of the present invention to develop an implant syringe of the above-mentioned kind such that it can be handled more easily.

In the implant syringe according to the invention, the syringe needle arrangement comprising a syringe needle, grip member and preparation receiving member is fixed by a blocking means until the plunger reaches the abutment during its advance movement. When the plunger has reached the front end position, the syringe needle arrangement is unblocked to that it can now be retracted.

The configuration of the invention has the effect that the implant syringe can be operated without the position of the hand being changed in such a manner that the plunger is first pushed forwards and that the syringe needle arrangement is then directly retracted up to an abutment. To this end the laterally projecting grip member of the implant syringe (after formation of the insertion channel) is e.g., gripped from behind with index finger and middle finger while pressure by which the plunger is advanced up to the abutment intended therefore is exerted on an end plate connected to the plunger by means of the thumb. Shortly before the abutment is reached or at the same time when the abutment is reached, the syringe needle arrangement is unblocked so that with the same position of the hand the grip member is now moved towards the end plate, with the syringe needle being retracted from the insertion channel while leaving the preparation behind. The implant syringe should remain with the front edge of its housing in contact with the patient's body.

Since the implant syringe need not be gripped around when handling the implant syringe between the advance movement of the plunger and the retraction of the needle, a handling of the implant syringe is considerably simplified. Further, the implant syringe is more stable during handling because a single position of the hand is maintained.

As for further details, the blocking means should comprise at least one, preferably two diametrically opposed spring arms that prevent(s) the rearward movement of the syringe needle arrangement in the unloaded initial state. To this end two spring arms can project into the interior of the guide means in which the syringe needle arrangement is seated, the arms being preferably positioned on a rear front wall of the syringe needle arrangement.

Furthermore, the plunger should be secured to an end plate which is provided with a sleeve surrounding the rear end section of the piston, the sleeve being preferably integrally molded onto the end plate. During the advance movement of the piston the sleeve abuts on the obliquely inwardly projecting spring arms shortly before reaching the abutment, thereby pressing the arms radially outwards, whereby the syringe needle arrangement is released for retraction.

It is within the scope of the invention that a different blocking means may also be provided for the syringe needle arrangement, said different blocking means being preferably movable due to the advance movement of the plunger into a release position.

Preferably a guide sleeve in which the arrangement of syringe needle, grip member and preparation receiving member is seated is provided as a guide means. Preferably, the syringe needle is firmly seated in a tubular holder which may be integrally formed with the grip member.

The at least one spring arm is expediently made integral with the guide sleeve. The at least one spring arm may be a small tab cut out from the sleeve wall, which (in the unloaded state) projects at an acute angle into the interior of the guide sleeve, the free end thereof facing the syringe needle arrangement.

BRIEF DESCRIPTION OF THE DRAWINGS

Further details of the invention will become apparent from the following description of a preferred embodiment of the implant syringe according to the invention and from the drawing, in which.

DETAILED DESCRIPTION OF THE DRAWINGS

Figure 4:
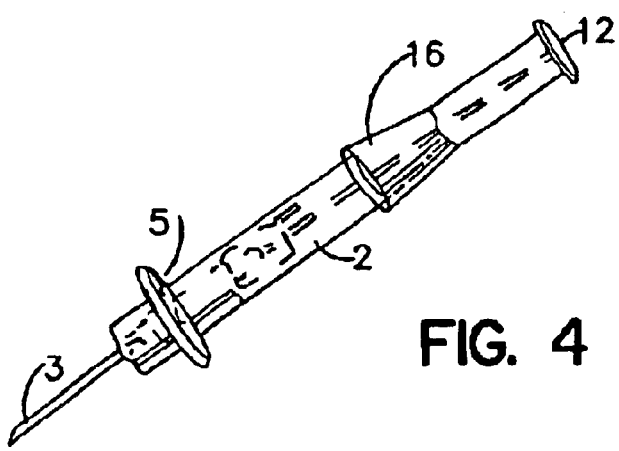
FIG. 4 is a side view of the implant syringe.

The implant syringe 1 includes an elongated guide sleeve 2 of a circular cross-section which has seated therein a syringe needle arrangement composed of the following components: a syringe needle 3 which is firmly seated in a tubular needle holder 34 which is integrally molded onto a grip member 5 surrounding the guide sleeve 2 (FIG. 4) and passes with two webs through longitudinally oriented slots of the guide sleeve 2, said webs forming the connection to the needle holder 4. A preparation receiving member 6 is seated with its front end section in a receiving chamber 7 behind the needle holder 4, the central receiving channel 8 for the preparation (not shown) being in alignment with the syringe needle 3. The axially rearward end of the syringe needle arrangement is formed by a cap 9 which comprises a rear front wall 10. Components 3, 4, 5, 6 and 9 are interconnected to perform a joint axial movement.

Furthermore, the implant syringe 1 comprises a rear plunger 11 which is centrally anchored in a rear end wall 12 and passes through a central bore in the rear front wall 10. The plunger 11 is in alignment with the channel 8 of the preparation receiving member 6 and with the syringe needle 3.

The end wall 12 is integrally connected to a sleeve 13 which surrounds the rear end section of the plunger 11. A spacer 16 which includes a slot 17 extending over the whole length thereof and which prevents the plunger 11 from being pushed forwards is arranged between the front edge 14 of the sleeve 13 and an outwardly oriented collar 15 of the guide sleeve 2.

Two spring arms 18 which project inwards at an acute angle and rest with their head ends 19 on the front wall 10 of the syringe needle arrangement are cut out from the wall of the guide sleeve 2. In the position shown in the figures, the spring arms block the syringe needle arrangement so that said arrangement cannot be retracted.

Figure 1:
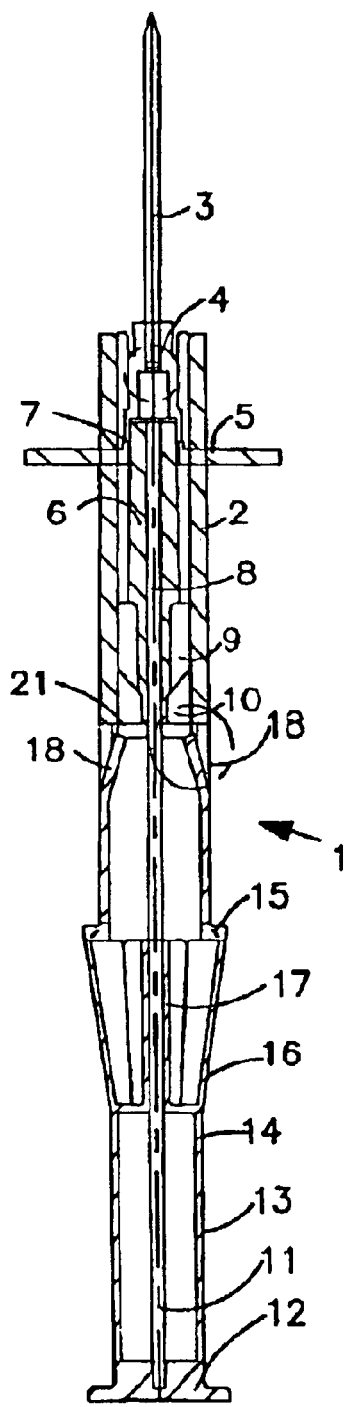
FIG. 1 shows a longitudinal section through the implant syringe.
Figure 2:
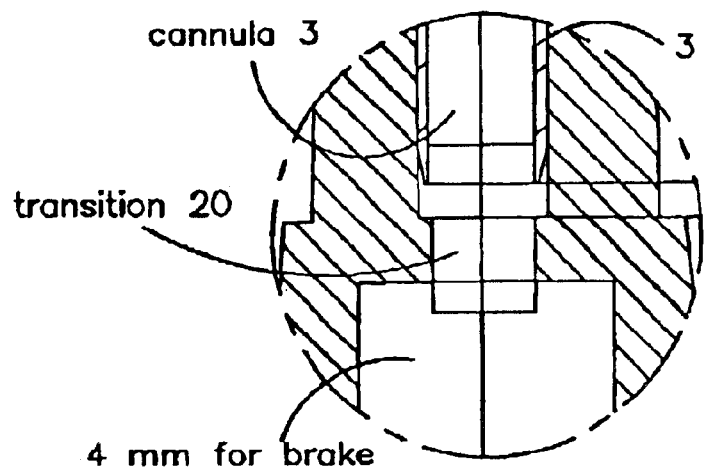
FIG. 2 shows a detail B of the implant syringe on an enlarged scale.
Figure 3:
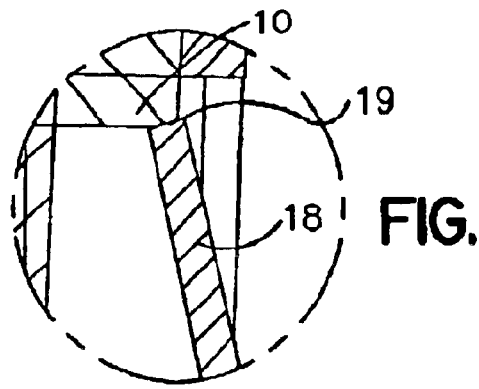
FIG. 3 shows a detail C of the implant syringe on an enlarged scale.

The implant syringe 1 is handled in the following way: First of all, the syringe needle 3 is pierced, for instance, into a patient's abdominal wall until the front edge of the needle holder 4 or the guide sleeve 2 comes to rest on the patient's body. The spacer 16 is then removed. Thereupon, the user grips behind the grip member 5 with his middle finger and index finger and presses with his thumb against the end plate 12, whereby the plunger 11 is pushed forwards, thereby pushing the preparation seated in the channel 8 into the channel of the syringe needle 3 up to the tip thereof. In this process the preparation (not shown) is pushed forwards through a transition 20 (FIG. 2) which has a slightly smaller diameter than the preparation and the subsequent channel of the syringe needle 3, so that the preparation cannot exit by itself from the syringe needle 3.

Towards the end of the advance movement the sleeve 13 abuts on the spring arms 18 and presses said arms radially outwards before the front edge 14 of the sleeve 13 reaches an abutment 21 of the guide sleeve 2. The elastically outwardly bent spring arms 18 now release the rear wall of the syringe needle arrangement.

While the user continues to exert an oppositely directed pressure on the end plate 12 and the grip member 5, the syringe needle arrangement is now retracted after the sleeve 13 has impinged on the abutment 21, the syringe needle leaving the preparation in the insertion channel. During this rearward movement the front edge of the guide sleeve 2 should remain in contact with the patient's body.

Since the grip position need not be changed during the above-described operation of the implant syringe 1 and since the advance movement of the plunger 11 is directly followed by the retraction of the syringe needle 3, the implant syringe can be handled not only very easily, but—in addition—the operation only requires a minimum amount of time.

What is claimed is:

1. An implant syringe comprising a syringe needle arrangement consisting of a syringe needle, a grip member and a preparation receiving member which are seated in a guide means for joint axial movement, and further comprising a plunger the advance movement of which is limited by an abutment such that a distance which is at least equal to the length of a preparation to be administered remains between the exit opening of the syringe needle and the head end of the plunger, characterized in that said syringe needle arrangement remains fixed by a blocking means (18) until the advance movement of the plunger is terminated by an abutment (21).

2. The implant syringe according to claim 1, characterized in that said blocking means comprises at least one spring arm (18) which in the unloaded initial state projects into the interior of the guide means (2).

3. The implant syringe according to claim 2, characterized in that the at least one spring arm rests in the unloaded initial state on a rear front wall (10) of the syringe needle arrangement.

4. The implant syringe according to claim 2, characterized in that said at least one spring arm (18) is cut out from said guide sleeve (2).

5. The implant syringe according to claim 1, said plunger being secured to an end plate which is provided with a sleeve surrounding the rear end section of said plunger, characterized in the during the advance movement of said plunger said sleeve (13) presses said at least one spring arm (18) is radially outwards, whereby said syringe needle arrangement is released.

* * * * *

UNITED STATES PATENT AND TRADEMARK OFFICE
CERTIFICATE OF CORRECTION

PATENT NO. : 6,837,865 B2
DATED : January 4, 2005
INVENTOR(S) : Roland Kneer

It is certified that error appears in the above-identified patent and that said Letters Patent is hereby corrected as shown below:

Column 3,
Line 11, "34" should be -- 4 --

Signed and Sealed this

Tenth Day of May, 2005

JON W. DUDAS
*Director of the United States Patent and Trademark Office*